United States Patent [19]

Wester

[11] Patent Number: 4,933,055
[45] Date of Patent: Jun. 12, 1990

[54] METHOD FOR PRODUCTION OF RADIOPHARMACEUTICALS USING ULTRASOUND

[75] Inventor: Dennis W. Wester, St. Louis, Mo.

[73] Assignee: Mallinckrodt, Inc., St. Louis, Mo.

[21] Appl. No.: 63,567

[22] Filed: Jun. 17, 1987

[51] Int. Cl.$^5$ .................. B01J 19/10; C07F 13/00; A61K 49/02

[52] U.S. Cl. .................. 204/157.62; 534/14; 424/1.1

[58] Field of Search .............. 534/14; 424/1.1; 204/157.62

[56] References Cited

U.S. PATENT DOCUMENTS 4,466,870 8/1984 Boudjouk et al. .............. 204/157.62
4,526,724 7/1985 Pillsbury .................. 534/14 X

OTHER PUBLICATIONS

European Journal of Nuclear Medicine, vol. 11, pp. 361–362, 1986.

Primary Examiner—John F. Terapane
Assistant Examiner—Virginia Caress
Attorney, Agent, or Firm—R. J. Klostermann; L. N. Goodwin

[57] ABSTRACT

A novel method for the production of bis(arene) technetium radiodiagnostic imaging agents is herein disclosed. The method consists of employing Fischer synthesis reactants in an ultrasonic bath. The products are virtually pure, thus lacking the severe degree of disproportionation which routinely occurs when partially alkylated bis(arene)technetium compounds are produced by thermally driven reactions.

7 Claims, 1 Drawing Sheet

METHOD FOR PRODUCTION OF RADIOPHARMACEUTICALS USING ULTRASOUND

BACKGROUND OF THE INVENTION

This invention relates to the production of bis(arene)-technetium complexes suitable for intravenous use in the radiodiagnosis of certain pulmonary and coronary metabolic functions.

Bis(arene)technetium complexes are of great practical clinical interest particularly in the diagnostic imaging of myocardial uptake. These compounds accumulate in normal heart tissue, as opposed to infarcted tissue, and the gamma rays emitted therefrom allow for the early identification of individuals at high risk of having heart attacks. An image of the heart tissue, taken for example with a scintillation camera, can be made inexpensively and expediantly. See co-pending U.S. application Ser. No. 739,511 filed May 31, 1985 by Wester et al.

However, the production of bis(arene)technetium complexes generally have received only cursory attention in the literature, usually being prepared for comparative studies with analagous manganese or rhenium compounds. The preparations of cyclopentadienyl and benzene derivatives were reported as early as 1961 (Huggins, D. K. and Kaesz, H. D., *J. Amer. Chem. Soc.*, 83:4474 [1961]; Fischer, E. O. and Schmidt, M. W., *Chem. Ber.*, 100:3782 [1967]; Baumgartner, F. et al., *Chem. Ber.*, 94:2198 [1961]; Palm, C. et al., *Tet. Lett.*, 1962(6) 253). Preparation of a hexamethylbenzene derivative was described by Fischer, E. O. and Schmidt, M. W., *Chem. Ber.*, 102:1954 (1969). Since that time the compounds have received no further attention in the literature.

Synthetic routes to the benzene and hexamethylbenzene complexes of technetium-99, as reported in the prior art, are long and arduous, making them unacceptable for commercial use. The prior art procedures generally use technetium tetrachloride (TcCl$_4$) as a starting material, a substance which is not easily prepared from Mo-99/Tc-99m generators. In the prior art procedures, TcCl$_4$ and benzene or hexamethylbenzene (along with other reagents) are heated in a sealed tube for 3 days or 24 hours, respectively. Since the half life of Tc-99m is 6 hours, it is apparent that most of the Tc-99m obtained from a generator will have decayed in the time required to prepare a technetium-arene complex by the prior art processes. More importantly, the partially methylated bis(arene) technetium complexes derived from starting materials such as pentamethylbenzene or tetramethylbenzene will undergo severe disproportionation into undesired impurities of other partially methylated benzenes at a rate as high as 30% or greater. This disproportionation or isomerization of the methylbenzenes occurs in the presence of aluminum chloride which is a necessary Fischer reactant. For example, when starting with pentamethylbenzene, both tetramethyl- and hexamethylbenzene are found in the reaction mixture in substantial amounts, indicating disproportionation or a isomerization of methyl groups during the reaction. The degree of disproportionation is believed to be virtually independent of the amount of aluminum chloride present, however. The disproportionation also occurs in the presence of aluminum powder and hydrogen chloride which are alternatives to the use of aluminum chloride although equivalent for purposes of this discussion. Previously, it was postulated that the presence of zinc and hydrogen chloride would diminish if not eliminate the disproportionation; however, in the presence of heat, improvements are still desired. Accordingly, it would be a substantial advancement in the art to prepare bis(arene)technetium complexes particularly the partially methylated variety at desirable high ratios of Tc-99m/Tc-99 of improved purity without disproportionation which are in turn of great practical clinical utility as radiodiagnostic imaging agents using the procedures of the prior art.

SUMMARY OF THE INVENTION AND DETAILED EMBODIMENTS

Figure 1:
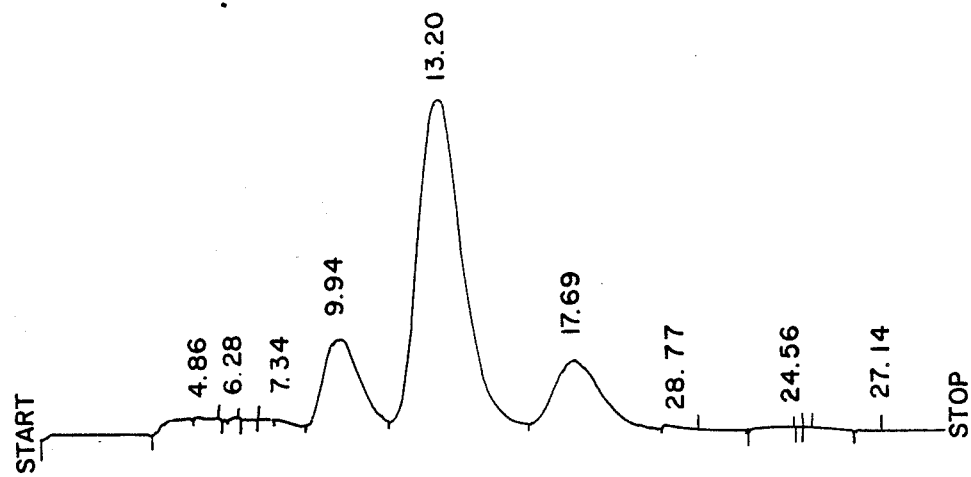
FIG. 1 is the high pressure liquid chromatographic result recorded and referred to in Example 1.

It is an object of the present invention to provide an efficient and effective improvement in the production of bis(arene)technetium complexes useful as myocardial perfusion imaging agents.

In accordance with the method of this invention, a mixture comprising a technetium-99m compound in an oxidation state higher than (I), a reducing agent, a metal halide which is capable of withdrawing halo ions, and a substituted benzene are reacted in an ultrasonic bath.

The technetium-99m compound in an oxidation state higher than (I) starting material can be any compound in which the technetium-99m is in a higher oxidation state than (I) such as the (IV) or (VII) oxidation state. Most commonly, the starting material will be of the formulas $^{99m}TcCl_4$ or $Na^{99m}TcO_4$, the sodium pertechnetate eluted from a Tc-99m generator.

The reducing agent is any known reducing agent which is capable of reducing Tc-99m in a higher oxidation state such s the Tc-99m (IV) or Tc-99m (VII) to Tc-99m (I) which does not interfere with the formation of the technetium-arene comlex. Preferably, the reducing agent is selected from the group consisting of Al,Zn,Fe and Sn. Most preferably, the reducing agent employed in the reaction is aluminum powder. The reducing agent is provided to the reaction mixture in a large molar excess to the amount of technetium compound present.

The metal halide is any compound which has the ability to remove halide ions form technetium. Preferred metal halides for this purpose are compounds of the formula AlX$_3$, wherein X is halogen, preferably chlorine or bromine. AlX$_3$ can be added directly to the reaction mixture or it can be formed in situ by providing appropriate amounts of aluminum powder and the corresponding HX compound, for example hydrogen chloride or hydrogen bromide. Other suitable metal halides for use in the method of the invention include the chloride salts of zinc, iron and tin. It is believed that the metal halide serves as a halide ion acceptor and is essential to the reaction in order to protect halide away from technetium by the formation of tetrachloroaluminate. When the starting material is TcCl$_4$, the need for halide acceptors is readily apparent. For NaTcO$_4$, we have found that the metal halide compound is still required. While not wishing to be bound by any particular theory of the reacton mechanism, it is believed that the pertechnetate undergoes an initial chlorination step, followed by reduction to the Tc(I) oxidation state and subsequent or simultaneous dechlorination. The amount of metal halide employed is generally in large molar excess to the amount of technetium compound employed in the reaction, for example, at least about 10 times the amount of technetium on a molar basis.

The substituted benzene raw materials of this invention may be substituted by one or more substituents such as alkyl, alkenyl, fluoroalkyl, and haloalkenyl having up to 12 carbon atoms; halo; carbamoyl; amido; amino; acyl; acyloxy; cyano; alkoxy; alkoxyalkyl; ester groups; keto groups; and aldehyde groups. The advantages of avoiding disproportionation are most pronounced in the bis-arenes in which benzene is partially methylated, however the following preferred starting materials may all be used in the process of this invention 1,2,3,5-$C_6H_2Me_4$; 1,3,5-$C_6H_3Me_3$; $C_6HMe_5$, p-cymene, t-butylbenzene; 1,3-diethylbenzene; 1,4-diethylbenzene; indan, toluene, m-xylene, 1,2,3,4-tetrahydronaphthalene; 1,3-diethyl-5-methylbenzene; methylbenzoate; and 5-isopropyl-m-xylene.

When substituted benzenes that are liquid at the reaction temperature are employed, the reaction can generally be carried out in the absence of solvent. Where a solvent is required or believed helpful, any solvent which is inert to the reactants and does not interfere with the reaction can be employed. Cyclohexane and hexafluorobenzene are preferred solvents. Aluminum bromide can be employed as the metal halide (halide acceptor) and solvent; however, it is not preferred as a solvent as much as unacceptable amounts of aluminum tend to be found in the product.

Extraction solvents or fluids, such as ether may be added at the end of the reaction to assist in extraction of the product, however, the impurities found herein under this invention may substantially negate the need for such assistance in extraction.

The reaction thus far to this point absent the use of sonification parallels in substantial part the reaction mechanism known in the art as the Fischer synthesis.

Nevertheless, the substantial improvements brought about in the process of this invention inure from the use of sonification to drive the reaction rather than heat. Although sonification or the use of ultrasonic baths as a labelling procedure for radiopharmaceuticals such as $^{123}$I or radioactive iodine have been known, suxh ultrasonic methods were not known to avoid the formation of labelled side products nor for increasing yields considerably absent the addition of extraneous constituents which are expensive and/or may detrimentally effect the particular functionality of the radiophearmaceutical. Previously, for example, thiosulfate was found to allow ultrasonic reaction to avoid the formation of radioactive iodine side products. See the *European Journal of Nuclear Medicine* (1986) Volume 11, pages 361–362. Such extraneous constituents like thiosulfate are surprisingly unnecessary in the present invention.

The ultrasonic bath in which the present invention may be conducted can be any commercially available bath, preferably 100 watt, 55 kilohertz. The reaction is conducted for any amount of time needed to complete tha same and as little as ½ inch of water may be employed for laboratory-size vials. As little as 30 minutes or less is the preferred time period although longer times may be employed if desired. The reaction will be seen to proceed at temperatures lower than 50° C. or as low as 40° C. completely and with substantially improved purity without having to add thiosulfate or other constituents.

After sonification, water may be added and the aqueous layer of the reaction mixture separated and filtered. The technetium labelled complexes of this invention are found to be of high purity devoid of any significant disproportionation as may be detected with any traditional chromatographic procedures.

EXAMPLE 1

The eluent from a commercial (Mallinckrodt) Tc-99m generator containing sodium pertechnetate and sodium chloride was dried to a solid on a rotary evaporator. Acetone (40 mL) was added to the solid, the mixture was lsurried gently and the acetone was evaporated. A second portion of acetone (40 mL) was added and evaporated as before. The remaining solid was slurried with acetone (10 mL) to produce a nearly salt-free solution of sodium pertechnetate (Tc-99m) in acetone, hereafter referred to as reconstituted pertechnetate. Reconstituted pertechnetate (1 mL) was placed in an oven-dried 10 mL serum vial. The vial was stoppered and sealed. The acetone was evaporated using standard Schlenk techniques to produe a vial containing sodium pertechnetate (TC-99m) in a dry state under an argon atmosphere; hereafter referred to as dried sodium pertechnetate (Tc-9.m). To the dried sodium pertechnetate (Tc-99m) under an argon atmosphere were added a miniature ($\sim \times 3$ mm) magnetic stir bar, 1,2,3,5-tetramethylbenzene (2 mL), aluminum powder (−40 mesh, $\sim 10$ mg) and a quantity of HCl gas sufficient to provide a purged mixture and one atmosphere of pressure. The vial was heated at 135° C. for 45 min. with stirring. The vial was cooled in ice water and opened. The reaction mixture was diluted with diethylether (2 mL) and hydrolyzed with water (1 mL) by vigorous shaking. The aqueous layer was separated and filtered through a 0.2 micron teflon membrane cartridge filter. The hydrolysis and extraction with water (1 mL) was repeated and the filtrates were combined. High pressure liquid chromatography (HPLC) of the filtrate using a reversed-phase PRP-1 column (Hamilton, 250 ×4.1 mm 10 micron) and a mobile phase of ethanol (33%), water (67%) and $KH_2PO_4$ (2 mM) at pH 3.5 and a flow rate of 0.8 mL/min. showed several peaks (FIG. 1).

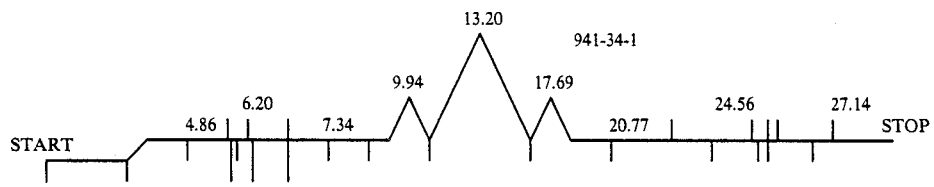

FIG. 1

The peak at 13.20 minutes represents the bis-(1,2,3,5-tetramethylbenzene)technetium(I) cation at only 68.9%, while the peaks at 9.94 and 17.69 mins. represent the (trimethylbenzene) (tetralethylbenzene) and (tetramethylbenzene) (pentamethylbenzene)technetium(I) cations at 15.2% and 15.8%, respectively. Disproportionation of the tetramethylbenzene to trimethyl-and pentamethylbenzene under the conditions of the reaction is shown by the gas chromatographic analysis of the organic layer from the reaction mixture. In the gas chromatogram, peaks corresponding to all three trimethylbenzene isomers and pentamethylbenzene are found in what was initially a nearly analytically pure sample of 1,2,3,5-tetramethylbenzene.

EXAMPLE II

Figure 2:
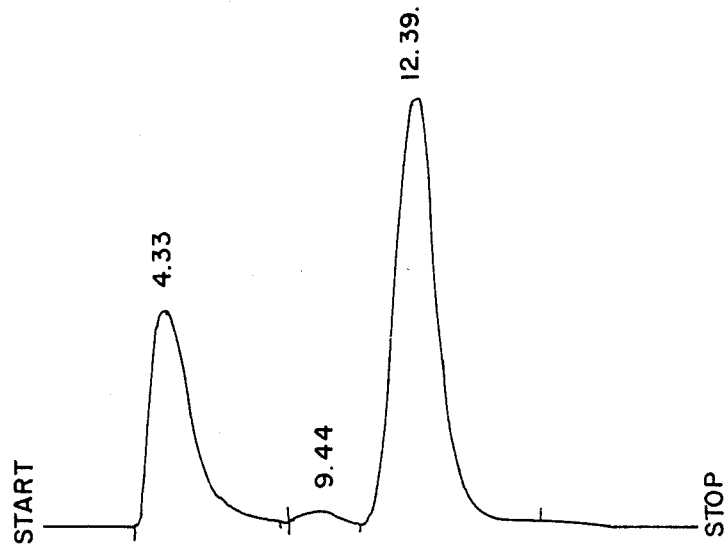
FIG. 2 is the high pressure liquid chromatographic result recorded and referred to in Example II.

Dried sodium pertechnetate (Tc-99m) was prepared as in Example 1. Cyclohexane (2 mL), 1,2,3,5-tetramethylbenzene (0.4 mL), aluminum powder (−40 mesh, ~10 mg) and HCl gas (1 atmosphere) were added to the vial which was then stoppered and sealed. The vial was placed in a commercial (Branson, 100 watt, 55 kHz) ultrasonic cleaner containing about 0.5 in. of water and sonicated for 30 min. during which the temnperature rose to 40° C. The vial was opened, water (1 mL) was added and the mixture was shaken. The aqueous layer was separated and filtered through a 0.2 micron teflon membrane cartridge filter. The hydrolysis and extraction with water (1 mL) was repeated and the filtrates were combined. HPLC analysis of filtrate using conditions identical to Example 1 showe only a slight impurity in the region where the bis(arene)technetium(I) cations appear (FIG. 2).

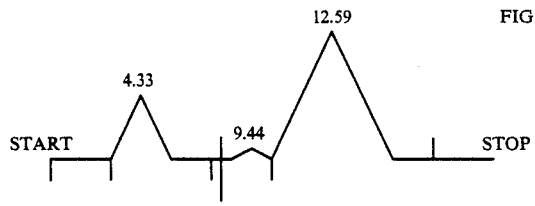

FIG. 2

The peak at 12.59 minutes corresponds to the bis-(1,2,3,5-tetramethylbenzene)technetium(I) cation at greater than 98% and a slight impurity (<2%) of the (trimethylbenzene) (tetramethylbenzene)- (9.44 minutes) and (tetramethylbenzene) (pentamethylbenzene)-technetium(I) cations. The peak at 4.33 min. in FIG. 2 is due to impurities which arise from the presence of air, water, or impure staring materials. Under rigorously controlled reaction conditions, this peak can be eliminated, and thus does not represent an umpurity inherent in the reaction. Disproportionation of the 1,2,3,5-tetramethylbenzene was not significant as judged by gas chromatographic analysis of the organic layer from the reaction mixture.

I claim:

1. A method for making bis(arene)technetium complexes useful as myocardial perfusion imaging agents which comprises reacting in an ultrasonic bath a mixture comprising a technetium-99m compound in an oxidation state higher than (I), a reducing agent, a metal halide, and a substituted benzene substituted by one or more substituents each selected from the group consisting of alkyl, alkenyl, alkynyl, fluoroalkyl and haloalkenyl having up to 12 carbon atoms; halo; carbomoyl; amido; amino; acyl; acyloxy; cyano; alkoxy; alkoxyalkyl; ester groups; keto groups; and aldehyde groups; whereby disproportionation is substantially negated without the need to add extraneous components and the reaction proceeds rapidly and completely at temperatures below about 50° C.

2. The method of claim 1 wherein the substituted benzene is selected from the group consisting of 1,2,3,5-$C_6H_2Me_4$; 1,3,5-$C_6H_3Me_3$; $C_6HMe_5$; p-cymene, t-butylbenzene; 1,3-diethylbenzene; 1,4-diethylbenzene; indan; tolune, m-xylene, 1,2,3,4-tetrahydronaphthalene; 1,3-diethyl-5-methylbenzene; methylbenzoate; and 5-isopropyl-m-xylene.

3. The method of claim 1, or 2 wherein the ultrasonic bath is a 55 kilohertz bath.

4. The method of claim 1 wherein the reducing agent is selected from the group consisting of aluminum, zinc, iron and tin in large molar excess.

5. The method of claim 1 wherein the reducing agent is aluminum powder.

6. The method of claim 1 wherein the metal halide is selected from the group consisting of $AlCl_3$ and $AlBr_3$ in a molar excess of at least 10 times the molar amount of technetium.

7. The method of claim 1 wherein the metal halide is formed in situ by providing appropriate amounts of aluminum powder and either hydrogen chloride or hydrogen bromide.

* * * * *

UNITED STATES PATENT AND TRADEMARK OFFICE
CERTIFICATE OF CORRECTION

PATENT NO. : 4,933,055

DATED : June 12, 1990

INVENTOR(S) : Dennis W. Wester

It is certified that error appears in the above-identified patent and that said Letters Patent is hereby corrected as shown below:

Column 2, line 40,
  "such s" should be --such as--;

Column 2, line 50,
  "halide ions form" should be --halide ions from--;

Column 2, line 61,
  "in order to protect" should be --in order to attract--;

Column 3, line 16,
  "materials may all be used" should be --materials all may be used--;

Column 4, line 23,
  "mixture was lsurried" should be --mixture was slurried--

Column 4, line 35,
  "technetate Tc9.m)." should be --technetate (Tc-99m).--

Column 4, line 37,
  "miniature ( x3mm)" should be --miniature (~1x3mm)--

UNITED STATES PATENT AND TRADEMARK OFFICE
CERTIFICATE OF CORRECTION

PATENT NO. : 4,933,055

DATED : June 12, 1990

INVENTOR(S) : Dennis W. Wester

It is certified that error appears in the above-identified patent and that said Letters Patent is hereby corrected as shown below:

Column 5, line 26, "Example 1 showe" should be
-- Example 1 showed --.

Signed and Sealed this

First Day of September, 1992

Attest:

DOUGLAS B. COMER

Attesting Officer

Acting Commissioner of Patents and Trademarks